(12) United States Patent
Swift et al.

(10) Patent No.: US 9,227,019 B2
(45) Date of Patent: Jan. 5, 2016

(54) PRE-FILLED SYRINGE IDENTIFICATION TAG

(71) Applicant: AMGEN INC., Thousand Oaks, CA (US)

(72) Inventors: Robert W. Swift, Fillmore, CA (US); Donald Wilson, Oxnard, CA (US)

(73) Assignee: AMGEN INC., Thousand Oaks, CA (US)

( * ) Notice: Subject to any disclaimer, the term of this patent is extended or adjusted under 35 U.S.C. 154(b) by 412 days.

(21) Appl. No.: 13/782,432

(22) Filed: Mar. 1, 2013

(65) Prior Publication Data

US 2014/0066857 A1  Mar. 6, 2014

Related U.S. Application Data

(60) Provisional application No. 61/694,762, filed on Aug. 29, 2012.

(51) Int. Cl.
*A61M 5/31* (2006.01)
*A61B 19/00* (2006.01)

(52) U.S. Cl.
CPC .............. *A61M 5/3135* (2013.01); *A61B 19/44* (2013.01); *A61B 2019/442* (2013.01); *A61B 2019/446* (2013.01); *A61B 2019/448* (2013.01);
(Continued)

(58) Field of Classification Search
CPC .................. A61M 5/3135; A61M 2205/6054; A61M 2205/60; A61M 2205/6081; A61M 2205/6072; A61B 19/44; A61B 2019/446; A61B 2019/442; A61B 2019/448; A61J 7/0445; A61J 1/035; A61J 7/0472

USPC .......................................................... 604/189
See application file for complete search history.

(56) References Cited

U.S. PATENT DOCUMENTS 5,256,154 A * 10/1993 Liebert et al. ................. 604/199
5,607,399 A    3/1997 Grimard et al.
(Continued)

FOREIGN PATENT DOCUMENTS

DE    102004046003    3/2006
WO    WO 2006/108026    10/2006
WO    WO 2011/039215    4/2011

OTHER PUBLICATIONS

International Search Report and Written Opinion, corresponding International Application No. PCT/US2013/054645, mailing date Oct. 17, 2013.
(Continued)

*Primary Examiner* — Manuel Mendez
(74) *Attorney, Agent, or Firm* — Marshall, Gerstein & Borun LLP (57) ABSTRACT

An assembly includes a pre-filled syringe including a barrel with a first end and a second, open end, a plunger disposed within the barrel and spaced between the first end and the second, open end, a product disposed in the barrel between the first end of the barrel and the plunger, and an outwardly-directed rim disposed about the barrel at the second, open end. In addition, the assembly includes an identification tag secured to the outwardly-directed rim of the barrel of the syringe with an outwardly-facing surface of the tag overlying the second, open end of the barrel, the tag having an identifier disposed on the surface of the tag, the identifier including data regarding the pre-filled syringe, the product disposed in the barrel, or both.

29 Claims, 3 Drawing Sheets

(52) U.S. Cl.
CPC .... *A61M2205/60* (2013.01); *A61M 2205/6054* (2013.01); *A61M 2205/6072* (2013.01); *A61M 2205/6081* (2013.01)

(56) References Cited

U.S. PATENT DOCUMENTS

| | | | |
|---|---|---|---|
| 5,667,495 | A | 9/1997 | Bitdinger et al. |
| 5,984,901 | A | 11/1999 | Sudo et al. |
| 6,808,513 | B2 | 10/2004 | Reilly et al. |
| D581,527 | S | 11/2008 | Jansen |
| 2004/0010233 | A1 | 1/2004 | Hjertman et al. |
| 2004/0168293 | A1 | 9/2004 | Shimazaki |
| 2008/0188814 | A1 | 8/2008 | Lavi-Loebl et al. |
| 2008/0243088 | A1* | 10/2008 | Evans ................. 604/246 |
| 2009/0216198 | A1 | 8/2009 | Salas |
| 2011/0253715 | A1* | 10/2011 | Phaneuf et al. ............ 220/212 |
| 2011/0282297 | A1 | 11/2011 | Westbye |
| 2011/0313395 | A1 | 12/2011 | Krulevitch et al. |
| 2012/0101446 | A1 | 4/2012 | Heald |

OTHER PUBLICATIONS

International Search Report and Written Opinion, corresponding International Application No. PCT/US2013/054645, mailing date Mar. 12, 2015.

B. Braun Needles and Syringes, B. Braun Medical Inc., Bethlehem, Pennsylvania, 2 pp. (2011).

Glass Prefillable Syringe Systems, Becton, Dickinson and Company, Franklin Lakes, New Jersey, 1 page (2012).

Prefilled Syringes: New Ideas for the New Decade, East Sussex, United Kingdom: ONdrugDelivery Publishing, 24 pp. (2010).

* cited by examiner

PRE-FILLED SYRINGE IDENTIFICATION TAG

BACKGROUND

This patent is directed to an identification tag, and, in particular, to an identification tag that is attachable to and removable from a pre-filled syringe.

The pre-filled syringe is a common device used for the delivery of pharmaceuticals to patients. The pre-filled syringe may be configured for use as a conventional syringe, with a needle at one end and a plunger rod at the other. Alternatively, the pre-filled syringe may be configured for use as part of an assembly, such as an auto-injector, for example.

During the manufacturing process, the empty syringes are filled and the plunger is put in place within the barrel. This pre-filled syringe may then be moved along the manufacturing line, shipped between manufacturing facilities, stored in a storage area, etc. before the pre-filled syringe is assembled into its final form (e.g., with a plunger rod or as part of an auto-injector) and placed into packaging that identifies the assembly and the product in the pre-filled syringe to the end user.

During the process of moving the pre-filled syringe along the line, between facilities, or into and out of storage, it is important to be able to distinguish one set of syringes from another, especially when the pre-filled syringe is being shipped from one manufacturing facility to another, the facilities being separated by hundreds or thousands of miles. Moreover, advances in process and inventory management require that considerable amounts of information be associated with each pre-filled syringe so that the pre-filled syringe may not only be distinguished from other syringes containing other pharmaceuticals, but so that the individual pre-filled syringe may be distinguished from other pre-filled syringes filled with the same pharmaceutical.

By their nature, syringes are difficult to mark. Most of the surface of the syringe is curved, which makes both the application of information to and reading of information from these surfaces problematic. As for those limited surfaces of the syringe, such as the finger flange, that may not be curved, they are so limited as to available or usable surface area that the amount of information that can be applied is generally insufficient to facilitate simple application and reading of the information applied to these areas. Also, the presence of silicone oil on the surfaces of the syringe may make certain forms of marking problematic. As to those marking methods that are not influenced by the presence of the oil, such as high-energy marking (e.g., laser etching), these methods may negatively affect the syringe barrel material or the product contained within the pre-filled syringe. On the other hand, if the pre-filled syringes were marked prior to filling, this may add further complexity to the inventory process control and the filling process control.

As set out in greater detail below, the present disclosure sets forth an improved identification tag embodying advantageous alternatives to the conventional devices and methods discussed above.

SUMMARY

According to an aspect of the present disclosure, an assembly includes a pre-filled syringe including a barrel with a first end and a second, open end, a plunger disposed within the barrel and spaced between the first end and the second, open end, a product disposed in the barrel between the first end of the barrel and the plunger, and an outwardly-directed rim disposed about the barrel at the second, open end. In addition, the assembly includes an identification tag secured to the outwardly-directed rim of the barrel of the syringe with an outwardly-facing surface of the tag overlying the second, open end of the barrel, the tag having an identifier disposed on the surface of the tag, the identifier including data regarding the pre-filled syringe, the product disposed in the barrel, or both.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

The present disclosure relates to an identification tag for use with a pre-filled syringe. The identification tag may be used to convey information relating to the contents of the pre-filled syringe prior to the assembly of the syringe with a plunger or in an auto-injector, for example. The information may be conveyed in a variety of methods, certain methods requiring additional equipment to be used to determine the information conveyed (e.g., a bar code reader or an RFID tag reader). According to certain embodiments, the tag may also provide a mechanism to ensure that the pre-filled syringe has not been intentionally or unintentionally tampered with, or that the tag itself has not been intentionally or unintentionally tampered with. Furthermore, the tag may provide the ancillary advantage of limiting or preventing access to the internal portion of the syringe which may limit or prevent intentional or unintentional contamination of and/or entry of particulate matter into the syringe.

Figure 1:
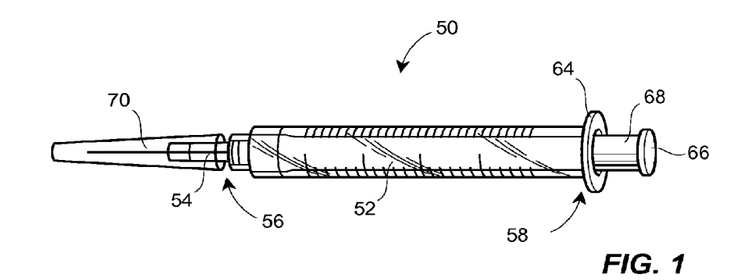
FIG. 1 is a side view of a pre-filled syringe.

As mentioned above, the identification tag may be particularly useful with a pre-filled syringe 50, such as is illustrated in FIG. 1, that includes a barrel 52 with a hub 54 at a first end 56 and a second, open end 58. The syringe may include a plunger 60 (see FIG. 5) disposed within the barrel 52 and spaced between the first end 56 and the second, open end 58. A product 62 (again, see FIG. 5), such as a pharmaceutical or medicament, is disposed in the barrel 52 between the first end 56 of the barrel 52 and the plunger 60. The syringe 50 may further include an outwardly-directed rim 64 disposed about the barrel 52 at or near the second, open end 58. This rim 64 may define a finger flange, for example, against which the user applies his or her forefinger and index finger at the same time the user applies his or her thumb to a thumb rest 66 on a plunger rod 68 to expel the product 62 from the syringe 50. Alternatively, a structure may be attached to the rim to define a finger flange for the assembled syringe 50. The syringe 50 may have additional features besides those mentioned (e.g., a needle 70 mounted or staked to the hub 54, a seal disposed between the plunger and the second end, etc.).

The identification tag is particularly for use with the syringe 50 when the plunger rod 68 is not attached to the plunger 60, which may occur during the process of filling the syringe 50 prior to assembly of the pre-filled syringe with a plunger rod 68 or as part of an auto-injector, for example. The identification tag is secured to the outwardly-directed rim 64 (which will be referred to as the finger flange throughout, for ease of reference and not by way of limitation) of the barrel 52 of the syringe 50 with an outwardly-facing surface of the tag overlying the second, open end 58 of the barrel 52. In certain embodiments, the tag may completely cover the interior of the barrel 52; in fact, the tag may even completely cover the finger flange 64. The tag may be made of a variety of materials, including metals, plastics, and combinations thereof. The tag has an identifier disposed on the surface of the tag, the identifier including data regarding the pre-filled syringe 50, the product 62 disposed in the barrel 52, or both. For instance, the identifier may identify the pharmaceutical name of the product 62 disposed in the barrel 52, its concentration, and/or the lot number associated with the syringe 50.

The identification tag may be expressed in a variety of embodiments, of which several are illustrated in the accompanying figures and discussed herein. Each of these embodiments may include features and variants of those features, certain features and variants being limited to a particular embodiment, while other features and variants may be common to or capable of being used or incorporated into all embodiments. While an attempt has been made to identify those features common to one or more of the embodiments or capable of being used or incorporated into one or more embodiments, this attempt should not be viewed as exhaustive.

Figure 2:
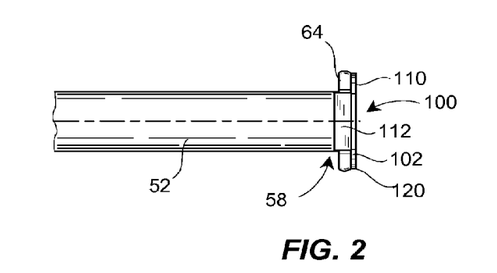
FIG. 2 is a side view of a first embodiment of a pre-filled syringe identification tag according to the present disclosure as assembled on a pre-filled syringe.
Figure 3:
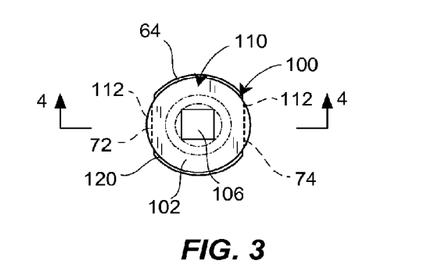
FIG. 3 is a plan view of the tag of FIG. 2 as assembled on a pre-filled syringe.
Figure 4:
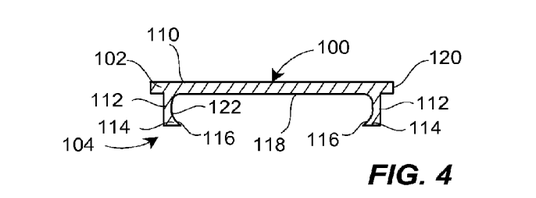
FIG. 4 is an enlarged, cross-sectional view of the tag taken about line 4-4 in FIG. 3.

Starting then with FIGS. 2-4, a first embodiment of the identification tag 100 according to the present disclosure is illustrated therein. The identification tag 100 includes a disk 102 and at least one fastener 104 (best seen in FIG. 4) attached to the disk 102. As illustrated in FIG. 3, in use the disk 102 overlies the second, open end 58 of the barrel 52, while the fastener 104 is attached to the rim 64 to secure the identification tag 100 to the rim 64 (and thus the syringe 50). In fact, as illustrated, the disk 102 completely covers the interior of the barrel 52. An identifier 106 may be disposed on the disk 102, for example by attaching the identifier 106 to the disk 102 or forming the identifier 106 on the disk 102 by printing or overt/covert marking, for example.

As will be recognized, the disk 102 according to the embodiment illustrated in FIGS. 2-4 takes the form of a flat, circular plate. The disk 102 is not limited to such a shape, however, as will be explained in greater detail below relative to FIG. 6, for example. However, as illustrated in FIGS. 2-4, and in particular FIG. 3, the disk 102 of this variant of the first embodiment is in the form of a circle having a diameter that is approximately equal to the diameter of the finger flange 64 of the pre-filled syringe 50 to which the tag 100 is attached, and thus also completely covers the finger flange 64. It will be recognized that it may be a slight misstatement to discuss the finger flange 64 has having a diameter, because opposing sides of the flange 64 (i.e., sections of the flange 64 on opposite sides of the barrel 52 of the syringe 50) may be clipped or formed in such a way to define a pair of opposing parallel edges 72, 74. In addition, the finger flange 64 may be not be circular in shape in any event (e.g., the flange 64 may be more oval that circular in shape). Consequently, it will be appreciated that the discussion of the disk 102 having a diameter that is approximately equal to the diameter of the finger flange 64 simply suggests that the disk 102 is large enough that the finger flange 64 appears to be completely covered by the disk 102 in an end-on view such as is illustrated in FIG. 3. According to other embodiments, the disk 102 may have a larger diameter or a slightly smaller diameter.

As mentioned previously, the disk 102 provides a surface 110 on which to dispose the identifier 106. In fact, as illustrated in FIG. 3, the disk 102 provides a sizable increase in the overall planar surface area to which one might dispose the identifier 106. That is, the cylindrical shape of the syringe 50 provides a generally curved surface (on the barrel 52) on which to dispose an identifier, which curvature may cause difficulties relative to the application or formation of the identifier to the syringe and/or relative to reading the identifier so applied or formed (e.g., by a bar code reader). On the other hand, the finger flange 64 may provide a planar surface, according to certain embodiments, but the planar surface is limited to the annular region disposed about the barrel 52, which presents its own limitations and challenges relative to the application and reading (e.g., formation of alpha-numeric information about a curve may make the information difficult to read visually, for example).

To hold the disk 102 in place over the second end 58 of the syringe 50, the tag 100 includes at least one fastener 104. As best seen in FIG. 4, the tag 100 includes at least two opposing arms 112 that depend from the disk 102 in a first direction. Each arm 112 has an inwardly-directed finger 114. The inwardly-directed fingers 114 attached to the at least two-opposing arms 112 point at each other and are spaced from the disk 102 to receive the rim 64 between opposing surfaces 116, 118 of the fingers 114 and the disk 102 to secure the identification tag 100 to the rim 64.

As illustrated, the two opposing arms 112 are attached to the surface 118 opposite the surface 110 on which the identifier 106 is disposed. As illustrated, the arms 112 are attached to the surface near a periphery 120 of the disk 102 on opposing sides of the disk 102 so that when the disk 102 is attached to the syringe 50, the arms 112 depend past the opposing parallel edges 72, 74 of the finger flange 64. As such, the finger flange 64 (and in particular, one of the opposing parallel edges 72, 74 of the finger flange 64) is received between the inwardly-directed finger 114 of the arm 112 and the surface 118 of the disk 102 to which the arms 112 are attached. In fact, as illustrated, the portion of the arm 112 (or at least an inner surface 122 thereof) between the surface 118 and the finger 114 may be shaped (e.g., curved) so as to be complementary to the shape of the edge 72, 74.

The arms 112 and fingers 114 may be formed in place about the edges 72, 74, by crimping for example. Alternatively, the tag 100, and in particular the arms 112, may be made of a material (e.g., metal or plastic) that permits the arms 112 to flex outwardly as the tag 100 is attached to the finger flange 64. The tag 100 may be applied to the finger flange 64 of the syringe 50 by aligning the disk 102 with the finger flange 64 and applying a force on the disk 102 in the direction of the finger flange 64, the arms 112 of the tag 100 deflecting outwardly to permit the fingers 114 to pass outward of the edges 72, 74 and then to return inwardly to secure the edges 72, 74 of the finger flange 64 between the fingers 114 and the surface 118. In such a case, the fastener 104 defined by the arms 112 may be described as a snap-tight or snap-on fastener. Even when the arms 112 return inwardly, the arms 112 may still be slightly flexed outward of their original position or state.

Of course, the arms 112 and fingers 114 may be shaped (as illustrated in FIG. 4) so as to permit the tag 100 to slide off of and on to the finger flange 64, with the finger flange 64 again secured between the fingers 114 and the surface 118. A tag 100 configured to provide this alternative mode of assembly with the syringe 50 would permit the tag 100 to be made of a material that does not permit the arms 112 to flex relative to the disk 102. Further, a tag 100 providing this alternative mode of assembly would afford an advantage, in that the tag 100 may be easily assembled with the syringe 50, and a disadvantage, in that the tag 100 may be separated from the syringe 50. The disadvantageous separation permitted by a tag 100 such as illustrated in FIGS. 2-4 that permits a slide-on mode of assembly may be limited through the variant illustrated in FIG. 5.

Figure 5:
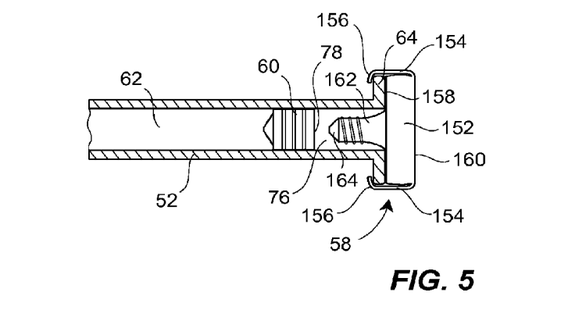
FIG. 5 is a partial, cross-sectional view of a variant of the first embodiment of the tag according to FIG. 2 as assembled on a pre-filled syringe.

FIG. 5 illustrates a variant of the tag 100 of FIGS. 2-4. Like the tag 100 of FIGS. 2-4, the tag 150 of FIG. 5 has a disk 152 with two opposing arms 154 that depend from the disk 152, each of the arms 154 having an inwardly-directed finger 156. The finger flange 64 is secured between the fingers 156 and a surface 158 of the disk 152, while an identifier may be disposed on an opposing surface 160. Unlike the tag of FIGS. 2-4, the tag of FIG. 5 has a post 162 that depends from the surface 158. As will be recognized from FIG. 5, the pre-filled syringe 50 used with the tag 150 includes a plunger 60 that is spaced from the second, open end 58 to define a recess 76 between an outer surface of the plunger 60 and the second, open end 58. In use, the post 162 is received in the recess 76 once the tag 150 is snapped onto the syringe 50, and may be vented so that introduction of the post 162 into the barrel 52 does not disturb the plunger 60.

As a consequence of the cooperation of the recess 76 and the post 162, it is not possible for the tag 150 of FIG. 5 to be slid on and off of the syringe 50. Instead, the tag 150 must be attached using a force applied to the tag 150 in the direction of the finger flange 64, and then a force generally in the opposite direction must be applied to deflect the arms 154 and thus to separate the tag 150 from the finger flange 64. The length of the post 162 may vary according to the depth of the recess 76, as well as in regard to the degree to which the post 162 is intended to resist a force applied at right angles across the finger flange 64, with the tag 150 illustrated as in FIG. 5. In any event, the cooperation between the barrel 52 and the post 162 prevents the tag 150 from being slid off of the end 58 of the syringe 58.

The post 162 may serve a further purpose as well. The length of the post 162 may be varied so that a free end 164 of the post 162 abuts or is in close proximity to a surface 78 of the plunger 60. With the end 164 abutting or in close proximity to the surface 78, the movement of the plunger 60 may be limited or prevented. It may be advantageous to limit the movement of the plunger 60 that may occur during air or high altitude truck shipment to limit or eliminate the possibility that the sterile product 62 will be exposed to the potentially non-sterile region between the plunger 60 and the second end 58 of the syringe 50. Consequently, in addition to the advantages mentioned above, the post 162 may provide additional advantages as well.

Figure 6:
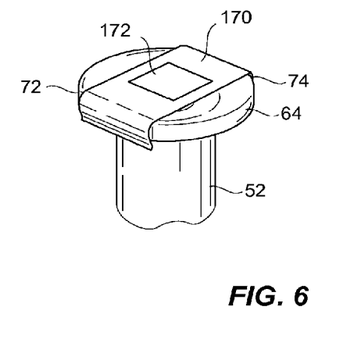
FIG. 6 is a perspective view of a further variant of the first embodiment of the tag according to FIG. 2 as assembled on a pre-filled syringe.

As mentioned above, while the disk 102 of the tag 100 illustrated in FIGS. 2-4 is defined by a circular plate, as will be seen with reference to FIG. 6, the disk is not so limited. For example, the disk may be defined a relatively rectangular plate or band 170 that depends between the opposing edges 72, 74 of the finger flange 64. In this case, while the band 170 completely covers the interior of the barrel 52, it does not completely cover the finger flange 64. While such a band 170 may not provide as much surface area as the circular plate of the disk 100 of FIGS. 2-4, the band 170 may provide surface area sufficient to apply an identifier 172 thereto, both in terms of overall surface area and in regard to the shape of the surface area (e.g., rectangular as opposed to annular). Other variations in the geometry of the disk are also possible, including one that follows the outline of the finger flange 64, for example.

As to the identifier, it will be recognized that identifier may be used to describe a unique object or a unique class of objects. That is, the identifier may provide data or information, such as product name and concentration, that distinguishes the pre-filled syringe from pre-filled syringes filled with other products. However, such an identifier may not identify the particular pre-filled syringe from other pre-filled syringes. Alternatively, the identifier may provide data or information that permits one pre-filled syringe to be distinguished from all other pre-filled syringes, either on a relative (e.g., at a particular point in time) or absolute basis. The use of a relative basis may provide for some reuse of the identifying information in the future.

As mentioned above, it will also be recognized that the identifier may take a variety of forms. For example, the identifier may include alphanumeric indicia disposed on the outwardly-facing surface of the tag. These indicia may be arranged in a format easily decipherable, such as the name of the product contained in the syringe. Alternatively, the indicia may be in the form of a code, such as a lot number, that may further be used to access an electronic database in which is stored information regarding the syringe and the product contained within the syringe.

In this regard, the identifier may be in a form that requires additional equipment to "read" the identifier. For example, the identifier may include one of a bar code, a radio frequency identifier, and an embedded integrated circuit. Such an identifier may require equipment, such as a bar code reader, RFID reader/receiver or compatible circuit, to "read" the identifier. Even then, the reading of the identifier may not immediately provide the information regarding the syringe or the product contained in the syringe: the identifier may include only such information that may be used to access an electronic database in which is stored information regard the syringe and the product contained within the syringe, for example. Additionally, the information read from the identifier may be encrypted, such that the information may need to be decrypted prior to its use or its use in accessing the aforementioned electronic database. While certain identifiers have been identified herein, this listing is not intended to be exhaustive, but illustrative, for still other identifiers that may be used may include microtaggants, microprint, UV-readable inks, and the like.

The identifier may be applied to the disk immediately prior to attaching the tag to the syringe. Alternatively, the tag could be attached to the syringe immediately after filling, and then the identifier may be disposed on the surface of the tag, with verification of the data or information conveyed by the identifier to follow immediately thereafter. As a further alternative, the tag may be attached to the syringe after visual/vision inspection.

Moreover, while the identifier 106 illustrated in FIGS. 2-4 does not cover the entire surface of the disk 102, it will be recognized that the identifier 106 may, in fact, cover the entire surface of the disk 102. The size of the identifier 106 relative to the surface of the disk 102 may vary from instance to instance of the tag 100 according to the present disclosure.

Figure 7:
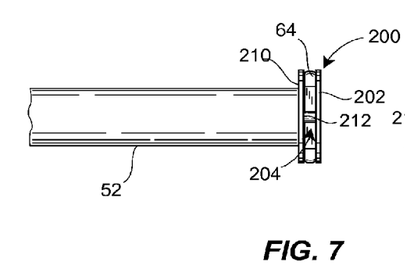
FIG. 7 is a side view of a second embodiment of a pre-filled syringe identification tag according to the present disclosure as assembled on a pre-filled syringe.
Figure 8:
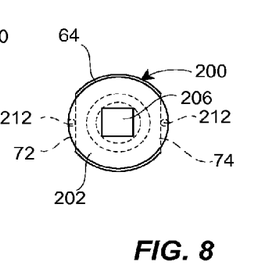
FIG. 8 is a plan view of the tag of FIG. 7 as assembled on a pre-filled syringe.
Figure 9:
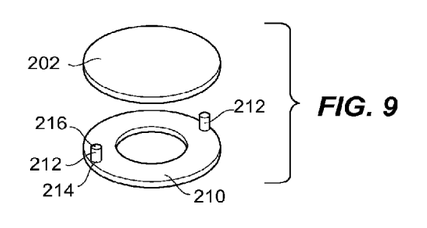
FIG. 9 is an exploded, perspective view of the tag of FIG. 7.
Figure 10:
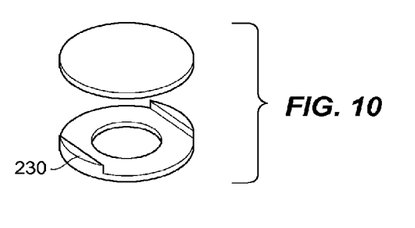
FIG. 10 is an exploded, perspective view of a variant of the tag of FIG. 7.

In the alternative to the embodiment illustrated in FIGS. 2-4 and its variants in FIGS. 5 and 6, a second embodiment of the pre-filled syringe identification tag 200 is illustrated in FIGS. 7-9, with a variant illustrated in FIG. 10. Similar to the embodiment of FIG. 2-6, the tag 200 includes a disk 202 on which an identifier 206 may be disposed. Further, a fastener 204 is provided to secure the disk 202 in place over the second end 58 of the pre-filled syringe 50. However, a different fastener is used than in the embodiment of FIGS. 2-6.

In particular, the tag 200 includes a ring 210, as best seen in FIG. 9. The ring 210 is received about the barrel 52 of the syringe 50, for example being introduced at the first end 56 and moved along the syringe 50 until it abuts the finger flange 64. At the same time, the disk 202 is disposed over the second, open end 58 of the barrel 52. One of the disk 202 and the ring 210 includes a connector that secures the ring 210 and the disk 202, to prevent removal of the disk 202 from the ring 210 with the finger flange 64 disposed therebetween to secure the identification tag 200 to the finger flange 64.

As illustrated, the connector may be in form of at least one arm 212 (e.g., two) depending from either the disk 202 or the ring 210. As illustrated in FIG. 9, the arms 212 depend from the ring 210. As further illustrated, the arms 212 pass to either side of the opposing edges 72, 74 of the finger flange 64, as best seen in FIGS. 7 and 8. The arms 212 each have first ends 214 attached to the ring 210 (e.g., integrally formed therewith) and second ends 216 that is attached to the disk 202 by ultrasonic welding, heat-staking or adhesive, for example. As a further alternative, a mechanical locking mechanism may be used. Once the arms 212 are attached to the disk 202, it may not be possible to remove the tag 200 from about the finger flange 64 and from the second end 58 of the pre-filled syringe 50 without the use of a tool.

Consequently, the tag 200 according to this embodiment may provide not only a mechanism by which an identifier 206 is associated with the pre-filled syringe 50, but also may be used to better determine if the tag 200 and/or plunger 60 has been tampered with intentionally or unintentionally. That is, if a tool is required to break or open the connectors, then a more direct conclusion may be reached that if the tag 200 is no longer attached to the pre-filled syringe 50 then it was removed on purpose, or that the tag 200 was removed with such force that it might have moved the plunger 60 or otherwise changed the contents of the syringe 50 (e.g., caused some of the product 62 to leave the syringe 50).

As will be recognized, it is convenient for the connector according to this embodiment (i.e., the arms 212) to be received on either side of the edges 72, 74 that define, in part, the finger flange 64. However, is it not a requirement that the arms 212 be received to either side of the edges 72, 74. In fact, the connectors may instead be disposed at various points about the periphery of the disk 202 or ring 210 to secure the ring 210 to the disk 202. According to such a variant, the number of connectors (e.g., arms 212) may be more than two. Alternatively, only a single connector may be used to secure ring 210 and disk 202.

As will also be recognized, while the arms 212 of the embodiment illustrated in FIGS. 7-9 are in the form of solid cylinders having a diameter that is less than the distance between the edge 72, 74 of the finger flange 64 and the periphery of the disk 202, this is simply one embodiment of the arms. For example, as illustrated in the variant of FIG. 10, arms 230 may be formed of greater cross-sectional area. The arms 230 of the variant of FIG. 10 have a cross-section such that they would extend from the periphery of the disk to the edge of the finger flange, and thus defined to be that portion of a circle between the periphery or perimeter and a chord of the same circle. Such an arm 230 provides a larger surface at a second end of the arm to be used in joining the arm (and thus the ring) to the disk.

While in all of the variants described in FIGS. 7-10, the disk and ring have a circular geometry, this need not be the case according to all variants of this embodiment. For instance, the disk 202 may be defined instead by a band, such as is illustrated in FIG. 6, which band extends or depends between the opposing edges 72, 74 of the flange 64 so that it may be attached to the arms 212 of the ring 210 to secure the disk 202 to the ring 210. Similarly, while the ring 210 is defined as an annular structure, the ring 210 may instead have a non-circular aperture at its center to receive the syringe 50 and/or a non-circular periphery. Further alternatives are also possible.

Furthermore, as explained above, it is possible to include features described relative to the embodiment of FIGS. 2-6 in regard to the embodiment of FIGS. 7-10. For example, the post 162 illustrated in regard to FIG. 5 may be included, depending from the disk 202 into the recess 76 defined between the plunger 60 at the second end 58 of the syringe 50. If such a post were to be included, it may then be possible to use a ring 210 that is not received entirely about the barrel 52, as illustrated in FIGS. 7-10, to prevent the tag 200 from being slid off and on the finger flange 64. For example, the ring 210 may have more of a U-shape or a C-shape, which shape may, without the post, permit the tag 200 to be slid off of the finger flange 64. However, in a variant wherein the post depends from the disk 202, even if the ring 210 has a U-shape or C-shape, the post will cooperate with the barrel 52 of the syringe 50 to oppose simply sliding the tag 200 off of and on to the syringe 50. It will be further recognized that such a post may also provide the advantages mentioned above relative to limiting the incidental movement of the plunger 60.

In addition, all of the remarks made relative to the identifier 106 above would apply with equal force to the identifier 206 of the embodiment of FIGS. 7-10.

Figure 11:
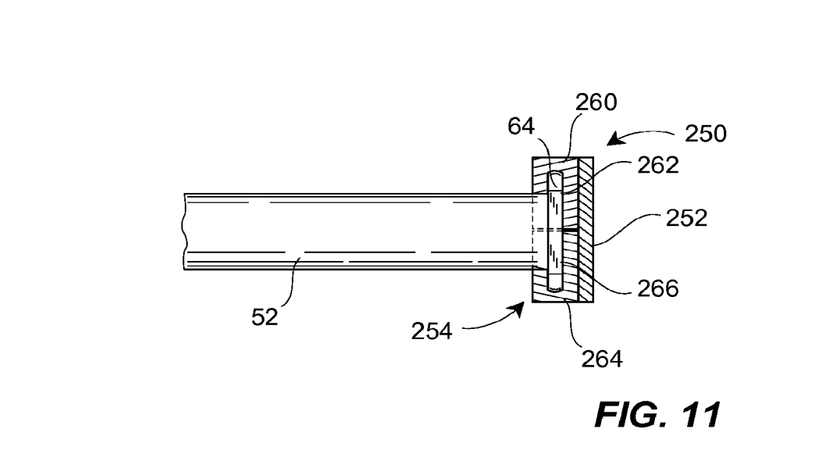
FIG. 11 is a partial, cross-sectional view of a third embodiment of the pre-filled syringe identification tag according to the present disclosure as assembled on a pre-filled syringe.
Figure 12:
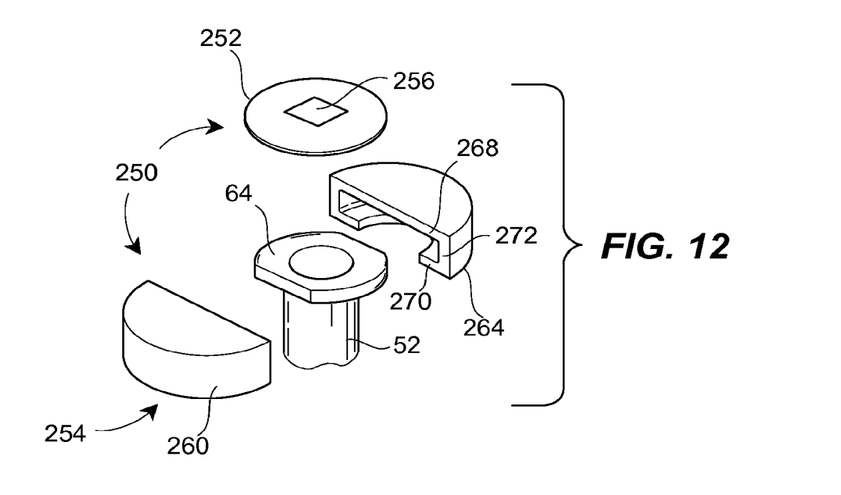
FIG. 12 is an exploded, perspective view of the tag of FIG. 11 in combination with a pre-filled syringe.

A still further embodiment of the tag is illustrated in FIGS. 11 and 12. Similar to the embodiments of FIGS. 2-6 and 7-10, the tag 250 of the embodiment of FIGS. 11 and 12 includes a disk 252 that defines a surface on which the identifier 256 is disposed. However, unlike the embodiments of FIGS. 2-6 and 7-10, the disk 252 of the embodiment of FIGS. 11 and 12 does not immediately abut the finger flange 64. Instead, the fastener 254 used to secure the disk 252 to the syringe 50 is disposed about the finger flange 64, and then the disk 252 is attached to the fastener 254.

As best seen in FIG. 11, the tag 250 includes a first section 260 having a slot 262 formed therein to accept a portion of the finger flange 64, and a second section 264 having a slot 266 formed therein to accept a portion of the finger flange 64. While the embodiment as illustrated and described includes two sections 260, 264, other embodiments may include more than two sections. As best seen in FIG. 11, the first and section sections 260, 264 are secured together with a portion of the finger flange 64 disposed in each of the first and second sections 260, 264 to secure the fastener 254, and hence the tag 250, to the finger flange 64. The disk 252 is then attached to the first and second sections 260, 264. As a consequence, the disk 252 is still disposed over the second, open end 58 of the barrel 50. In addition, the disk 252 may secure or further secure the first and second sections 260, 264 together.

As illustrated in FIGS. 11 and 12, each of the first and second sections 260, 264 has a C-shape. Moreover, each of the first and second sections 260, 264 includes the slot or recess 262, 266 formed therein that defines half of a space in which the finger flange 64 is disposed when the tag 250 is assembled (see FIG. 11). The finger flange 64 is trapped in the space with the first and second sections 260, 264 secured to each other, which secures the tag 250 to the pre-filled syringe 50 and which also may also act as a tamper-proof seal at the second end 58 of the syringe 50.

In particular, each C-shaped section 260, 264 includes a first, or upper, wall 268 and a second, or lower wall 270 (illustrated relative to section 264 in FIG. 12), the reference to upper and lower being with reference to the illustration of FIG. 12 and not by way of limitation but for ease of reference. The upper and lower walls 268, 270 are joined by a peripheral wall 272, which runs about an outer periphery of the section 264. As illustrated, when the two sections 260, 264 are joined, the peripheral wall 272 entirely surrounds the finger flange 64. However, it will be appreciated that the peripheral wall 272 may be discontinuous, such that the wall 272 is disposed about, but does not entirely surround the finger flange 64. When the peripheral wall 272 does entirely surround the finger flange 64, the finger flange 64 may be encased by or enclosed within the tag 250 when the tag 250 is fully assembled.

As illustrated, the upper wall 268 is semi-circular, while the lower wall 270 defines half of an annulus. Consequently, when the first and second sections 260, 264 are assembled, the upper walls 268 of the first and second sections form a circular plate, while the lower walls 270 form a ring. In this sense, the connector of the tag 250 of the embodiment of FIGS. 11 and 12 is similar to that of the tag 200 of FIGS. 7-10: the finger flange 64 is disposed between opposing surfaces of a circular-shaped wall or disk and an annular-shaped ring. However, unlike the ring 210 of the embodiment of FIGS. 7-10, the structures 260, 264 forming the comparable ring in the embodiment of FIGS. 11 and 12 do not need to be passed along the entire syringe 50.

The upper wall of the first and second sections 260, 264 of the tag 50 according to FIGS. 11 and 12 define, as mentioned above, a circular plate having a surface to which the disk 252 is attached, the attachment of the disk 252 to the sections 260, 264 optionally securing the sections 260, 264 together. It will be recognized that the first and second sections 260, 264 need not define a circular plate to which the disk 252 is attached; for example, the upper walls 268 of the first and second sections 260, 264 may define an annular-shaped ring instead. In fact, the upper wall 268 may be removed altogether according to certain embodiments, with the disk 252 being attached to a first, upper edge of the peripheral wall 272 instead. According to such an embodiment, the two sections 260, 264 would be very similar in structure and function, when assembled, to the ring 210/arms 212 described according to the embodiment of FIGS. 7-10.

As to variants relative to this embodiment, it will be recognized that, for example, all of the discussion relative to the identifier above may be applied to this embodiments as well.

As will be recognized also, the devices according to the present disclosure may have one or more advantages relative to conventional technology, any one or more of which may be present in a particular embodiment in accordance with the features of the present disclosure included in that embodiment. The identification tag according to the present disclosure provides a sizable amount of usable surface on which to apply an identifier. This is done in such a manner that this surface may be planar, which further simplifies the application of the identifier, as well as the process of reading the identifier, which reading may be required at numerous stations or checkpoints along an assembly line or when the pre-filled syringe to which the tag is attached is moved into and out of storage, or between facilities. Furthermore, according to certain embodiments disclosed herein, the identification tag may be configured in such a fashion that removal of the tag, once attached to the pre-filled syringe, is so difficult that the absence of the tag is suggestive of tampering either with the tag, the syringe or both. For that matter, even if the tag is not entirely removed from the syringe, damage to the tag may be suggestive to tampering, intentional or unintentional, with the tag, the syringe or both. Moreover, the tag may limit or prevent access to the internal portion of the syringe (e.g., the recess 76 between the plunger 60 and the second end 58 of the syringe 50) which may limit or prevent intentional or unintentional contamination and/or entry of particulate matter. Other advantages not specifically listed herein may also be recognized as well.

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, that would still fall within the scope of the claims defining the invention.

It should also be understood that, unless a term is expressly defined in this patent using the sentence "As used herein, the term '________' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

We claim:

1. An assembly comprising:
   a pre-filled syringe including a barrel with a first end and a second, open end, a plunger disposed within the barrel and spaced between the first end and the second, open end, a product disposed in the barrel between the first end of the barrel and the plunger, and an outwardly-directed rim disposed about the barrel at the second, open end; and an identification tag secured to the outwardly-directed rim of the barrel of the syringe with an outwardly-facing surface of the tag overlying the second, open end of the barrel, the tag having an identifier disposed on the surface of the tag, the identifier including data regarding the pre-filled syringe, the product disposed in the barrel, or both, wherein the identification tag comprises a ring that is received about the barrel and a disk that is disposed over the second, open end of the barrel, the ring secured to the disk with the rim disposed therebetween to secure the identification tag to the rim.

2. The assembly according to claim 1, wherein the identification tag comprises a disk that overlies the second, open end of the barrel and at least one fastener attached to the disk and the rim to secure the identification tag to the rim.

3. The assembly according to claim 2, wherein the at least one fastener comprises at least two opposing arms that depend from the disk, each arm having an inwardly-directed finger, the inwardly-directed fingers pointing at each other and spaced from the disk to receive the rim between opposing surfaces of the fingers and the disk to secure the identification tag to the rim.

4. The assembly according to claim 3, wherein each arm is made of a material to permit the arms to flex outwardly and return inwardly, and the at least one fastener is a snap-tight fastener.

5. The assembly according to claim 1, wherein the plunger is spaced from the second, open end to define a recess between a surface of the plunger and the second, open end, and wherein the tag includes a post that is received in the recess.

6. The assembly according to claim 5, wherein the post has an end that abuts or is in close proximity to a surface of the plunger.

7. The assembly according to claim 1, wherein one of the disk and the ring has at least one arm depending therefrom, the arm having a first end attached to the disk and a second end attached to the ring.

8. The assembly according to claim 1, wherein the ring is received entirely about the barrel.

9. The assembly according to claim 1, wherein the tag comprises a first section having a slot formed therein to accept a portion of the rim, and a second section having a slot formed therein to accept a portion of the rim, the first and section sections secured together with a portion of the rim disposed in each of the first and second sections to secure the identification tag to the rim.

10. The assembly according to claim 9, wherein the tag comprises a disk attached to the first and second sections with the disk disposed over the second, open end of the barrel.

11. The assembly according to claim 10, wherein the disk is attached to the first and second sections to secure the first and second sections together.

12. The assembly according to claim 9, wherein the first and second sections are each a C-shaped section, and the first and second sections define a space with the rim trapped therein when the first and second sections are secured to each other.

13. The assembly according to claim 1, wherein the tag completely covers an interior of the barrel of the syringe to limit access to the interior of the barrel.

14. The assembly according to claim 1, wherein the identifier comprises alphanumeric indicia disposed on the outwardly-facing surface of the tag.

15. The assembly according to claim 1, wherein the identifier comprises one of a bar code, a radio frequency identifier, an embedded integrated circuit, microtaggants, microprint, and UV-readable inks.

16. The assembly according to claim 1, wherein the rim comprises a finger flange.

17. The assembly according to claim 16, wherein the tag completely covers the finger flange.

18. The assembly according to claim 16, wherein the tag completely covers the finger flange.

19. An assembly comprising:
a pre-filled syringe including a barrel with a first end and a second, open end, a plunger disposed within the barrel and spaced between the first end and the second, open end, a product disposed in the barrel between the first end of the barrel and the plunger, and an outwardly-directed rim disposed about the barrel at the second, open end; and an identification tag secured to the outwardly-directed rim of the barrel of the syringe with an outwardly-facing surface of the tag overlying the second, open end of the barrel, the tag having an identifier disposed on the surface of the tag, the identifier including data regarding the pre-filled syringe, the product disposed in the barrel, or both, wherein the tag comprises a first section having a slot formed therein to accept a portion of the rim, and a second section having a slot formed therein to accept a portion of the rim, the first and section sections secured together with a portion of the rim disposed in each of the first and second sections to secure the identification tag to the rim.

20. The assembly according to claim 19, wherein the identification tag comprises a disk that overlies the second, open end of the barrel and at least one fastener attached to the disk and the rim to secure the identification tag to the rim.

21. The assembly according to claim 19, wherein the identification tag comprises a ring that is received about the barrel and a disk that is disposed over the second, open end of the barrel, the ring secured to the disk with the rim disposed therebetween to secure the identification tag to the rim.

22. The assembly according to claim 21, wherein the ring is received entirely about the barrel.

23. The assembly according to claim 19, wherein the tag comprises a disk attached to the first and second sections with the disk disposed over the second, open end of the barrel.

24. The assembly according to claim 23, wherein the disk is attached to the first and second sections to secure the first and second sections together.

25. The assembly according to claim 19, wherein the first and second sections are each a C-shaped section, and the first and second sections define a space with the rim trapped therein when the first and second sections are secured to each other.

26. The assembly according to claim 19, wherein the tag completely covers an interior of the barrel of the syringe to limit access to the interior of the barrel.

27. The assembly according to claim 19, wherein the identifier comprises alphanumeric indicia disposed on the outwardly-facing surface of the tag.

28. The assembly according to claim 19, wherein the identifier comprises one of a bar code, a radio frequency identifier, an embedded integrated circuit, microtaggants, microprint, and UV-readable inks.

29. The assembly according to claim 19, wherein the rim comprises a finger flange.

* * * * *